(12) United States Patent
Ponzi

(10) Patent No.: US 6,254,568 B1
(45) Date of Patent: Jul. 3, 2001

(54) DEFLECTABLE CATHETER WITH STRAIGHTENING ELEMENT

(75) Inventor: Dean M. Ponzi, Glendora, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 09/371,595

(22) Filed: Aug. 10, 1999

(51) Int. Cl.[7] .................................................. A61M 37/00
(52) U.S. Cl. ............................................................ 604/95
(58) Field of Search ........................... 604/95, 104, 107, 604/170, 524, 525, 526, 528, 530, 534, 535

(56) References Cited

U.S. PATENT DOCUMENTS

| | | | |
|---|---|---|---|
| 3,890,977 | 6/1975 | Wilson | 128/418 |
| 4,984,581 | 1/1991 | Stice | 128/772 |
| 5,209,784 | 5/1993 | Hurley et al. | 604/158 |
| 5,269,752 | 12/1993 | Bennett | 604/28 |
| 5,325,845 * | 7/1994 | Adair | 604/95 |
| 5,357,979 | 10/1994 | Imran | 128/772 |
| 5,383,923 | 1/1995 | Webster, Jr. | 607/125 |
| 5,531,685 * | 7/1996 | Hemmer et al. | 604/95 |
| 5,531,686 * | 7/1996 | Lundquist et al. | 604/95 |
| 5,681,344 | 10/1997 | Kelly | 606/194 |
| 5,820,591 * | 10/1998 | Thompson et al. | 604/95 |
| 5,910,129 * | 6/1999 | Koblish et al. | 604/95 |
| 6,033,378 * | 3/2000 | Lundquist et al. | 604/95 |

* cited by examiner

Primary Examiner—Manuel Mendel
(74) Attorney, Agent, or Firm—Christie, Parker & Hale, LLP

(57) ABSTRACT

The present invention provides a deflectable catheter having a catheter body, a tip section attached at a distal end of the catheter body and a control handle attached at a proximal end of the catheter body. A puller wire, anchored at its proximal end to the control handle and at its distal end to the tip section is provided in the catheter for deflecting the tip section. Longitudinal movement of the puller wire relative to the catheter body, resulting in the deflection of the tip section, is accomplished by a suitable manipulation of the control handle. To eliminate the "residual tip curve" problem arising out of the deflection, and especially repeated deflection, of the tip section a straightening element is carried by the catheter tip section. The straightening element consists of a short section of a flexibly resilient material and may be any suitable shape. The material of the straightening element is capable of returning to its original shape after plastic deformation. A straightening element of Nitinol wire having a circular cross-section with a diameter in the range of about 0.010 inches to about 0.020 inches, and preferably a diameter of about 0.014 inches is preferred.

18 Claims, 2 Drawing Sheets

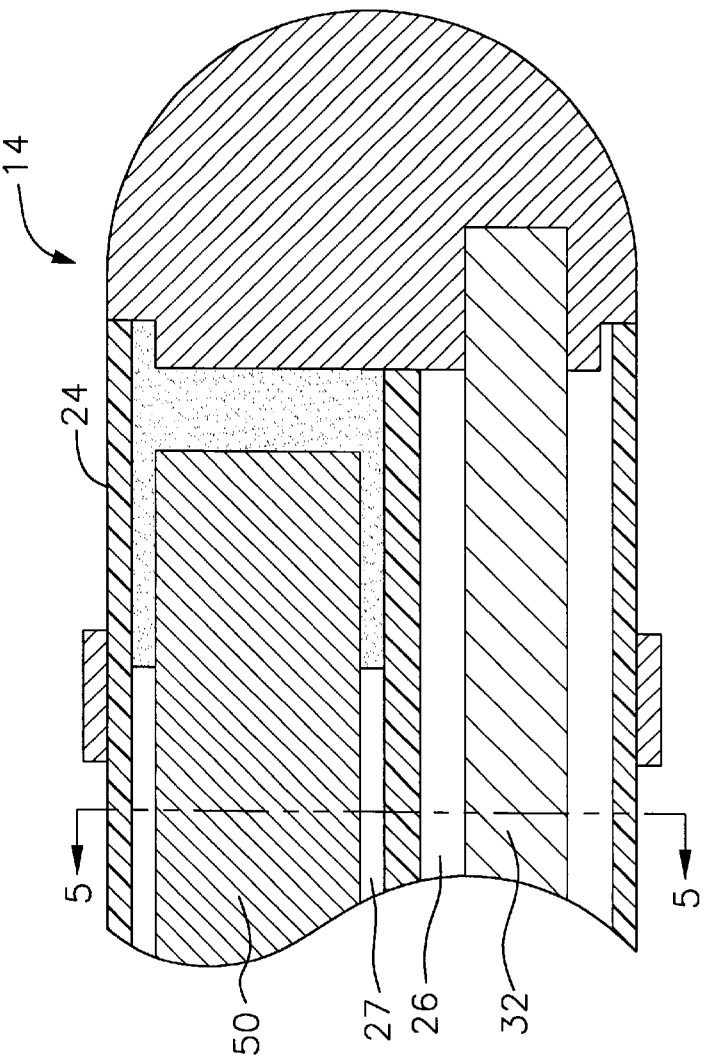
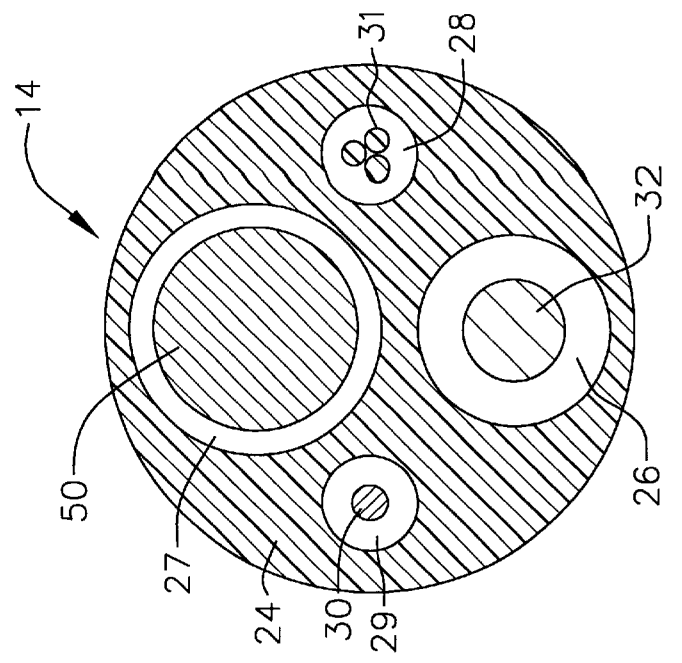

DEFLECTABLE CATHETER WITH STRAIGHTENING ELEMENT

FIELD OF THE INVENTION

This invention relates to a deflectable catheter, and particularly to a deflectable electrode catheter having a straightening element.

BACKGROUND OF THE INVENTION

Steerable or deflectable tip cardiovascular catheters are useful in many applications, being a marked improvement over catheters with fixed tips. They are especially useful in the field of electrophysiology for performing radio-frequency ablation of cardiac tissue to interrupt abnormal electrical pathways in the heart. Typically, ablation catheters carry one or more electrodes at their distal end. A steerable catheter assists the physician in guiding the distal end of the catheter so that the electrodes can be properly aligned with the tissue to be ablated.

There are presently several useful designs for steerable tip catheters. Such a catheter generally has a control handle at its proximal end for controlling deflection of the tip in one or more directions. For example, U.S. Pat. No. RE 34,502, the disclosure of which is incorporated herein by reference, describes a catheter having a control handle comprising a housing having a piston chamber at its distal end. A piston is mounted in the piston chamber and is afforded lengthwise movement. The proximal end of the elongated, tubular catheter body is attached to the piston. A puller wire, typically made of stainless steel, is attached to the housing and extends through the piston, through the catheter body and into an off-axis lumen in the catheter tip section. The distal end of the puller wire is anchored in the tip section of the catheter. In this arrangement, lengthwise movement of the piston relative to the housing results in deflection of the catheter tip section.

A known disadvantage of the deflectable catheters is that after deflection, and particularly after repeated deflections in one direction, the tip tends to maintain a residual curve in that direction. In other words, the tip is unable to return to its original straight orientation when the deflecting force is removed. This is a result of the deformable nature of the material of the tip section and particularly of the stainless steel puller wire.

SUMMARY OF THE INVENTION

The present invention provides a deflectable catheter which overcomes the residual tip curve problem of known deflectable catheters.

In accordance with the present invention, there is provided a deflectable catheter having a catheter body, a tip section attached at the distal end of the catheter body and a control handle attached at the proximal end of the catheter body. The catheter body comprises at least one lumen extending therethrough, preferably a single central lumen. The tip section comprises at least one lumen, preferably at least two lumens, extending therethrough in communication with the lumen(s) of the catheter body. A puller wire is anchored at its proximal end to the control handle and extends through a lumen of the catheter body and tip section and is anchored at its distal end to the tip section. Longitudinal movement of the puller wire relative to the catheter body, accomplished by a suitable manipulation of the control handle, results in the deflection of the tip section.

To eliminate the "residual tip curve" problem arising out of the deflection, and especially repeated deflection, of the tip section, a straightening element is carried by the catheter tip section. The straightening element is made from a short section of a flexibly resilient material and may be any suitable shape. The material of the straightening element must have shape memory, i.e., be capable of substantially returning to its original shape after plastic deformation. Preferred elements include rods or wires having a circular cross-section and bars or plates having square or rectangular cross-sections. The diameter or cross-sectional width of the straightening element depends upon the material used. In a preferred embodiment, the straightening element is made of Nitinol wire having a circular cross-section with a diameter in the range of about 0.010 inches to about 0.020 inches, and preferably a diameter of about 0.014 inches. In an alternative embodiment, the straightening element may be made of a resilient plastic such as Peek.

In a preferred embodiment, the distal end of the straightening element is fixedly attached to or adjacent to the distal end of the tip section and extends proximally through the tip section and into the distal end of the catheter body wherein the proximal end of the straightening element is fixedly attached. Alternatively, the straightening element can be fixedly attached to the catheter at one of its ends and unattached at its other end. It is understood that the straightening element may be anchored completely within the tip section, i.e., not extending into the catheter body, if desired. The straightening element can be disposed in the same lumen as the puller wire, or alternatively, an additional lumen could be provided for carrying the straightening element separately from the puller wire. Preferably the puller wire and straightening elements are in diametrically opposed off-axis lumens in the catheter tip section.

When the catheter tip is deflected by applying a force to the puller wire, the straightening element deflects with the tip. When the force is removed from the puller wire, the resiliency of the straightening element biases the catheter tip section back towards its initial straight position so that the tip section has less and preferably no "residual tip curve." The straightening element is particularly useful in unidirectional catheters using stainless steel puller wires. However, the use of straightening elements is also applicable to bi-directional and multi-directional steerable catheters.

DESCRIPTION OF THE DRAWINGS

These and other features of the advantages of the present invention will be better understood by reference to the following detailed description when considered in conjunction with the accompanying drawings wherein:

FIG. 4 is a side cross-sectional view of the distal end of the tip section of an embodiment of the present invention.

FIG. 5 is a transverse cross-sectional view of an embodiment of the present invention.

DETAILED DESCRIPTION OF THE INVENTION

Figure 1:
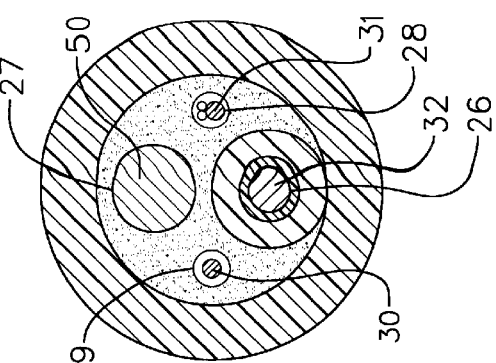
FIG. 1 is a side view of an embodiment of the catheter of the invention.
Figure 2:
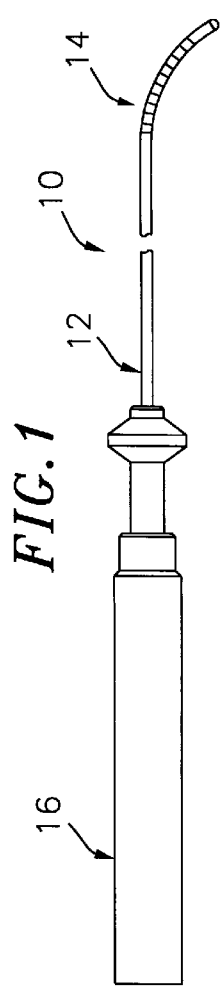
FIG. 2 is a side cross-sectional view of the junction of the catheter body and tip section of an embodiment of a catheter according to the invention.
Figure 3:
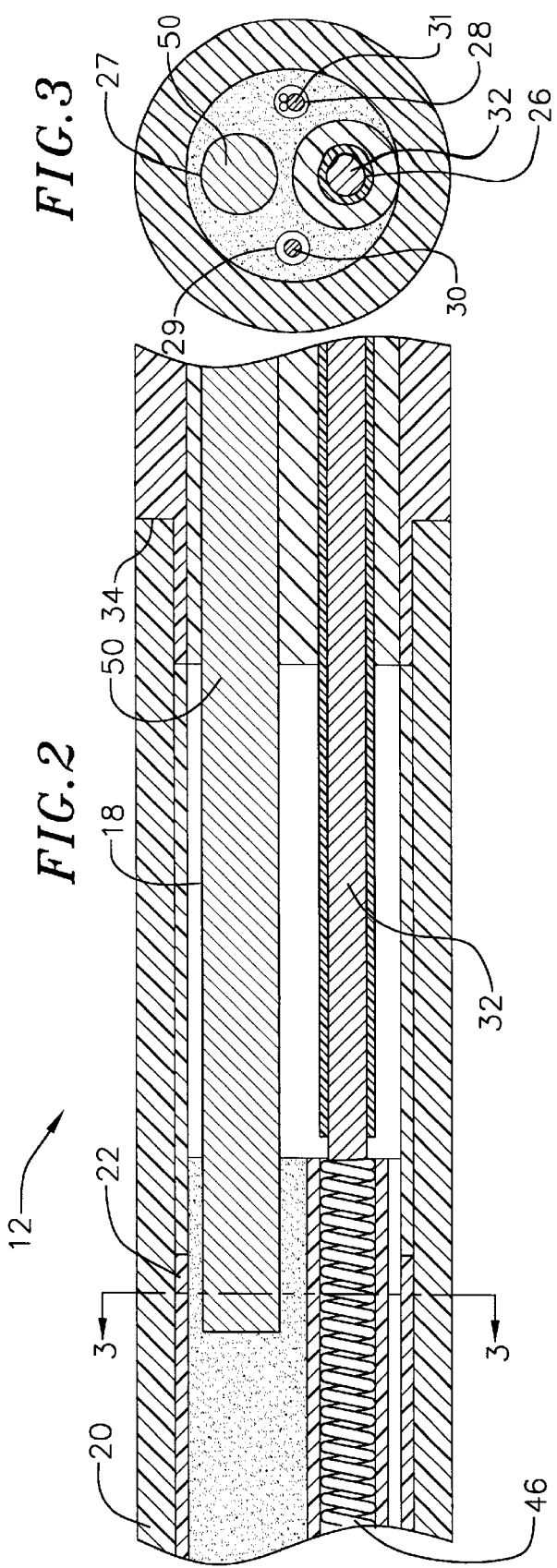
FIG. 3 is a transverse cross-sectional view of the catheter body shown in FIG. 2 taken along line 3—3.

In a particularly preferred embodiment of the invention, there is provided a steerable deflectable catheter having a straightening element, as shown in FIGS. 1–3. The catheter 10 comprises an elongated catheter body 12 having proximal and distal ends, a tip section 14 at the distal end of the catheter body 12, and a control handle 16 at the proximal end of the catheter body 12.

As shown in FIG. 2, the catheter body 12 comprises an elongated tubular construction having a single axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 preferably comprises an imbedded braided mesh of stainless steel or the like to increase torsional stiffness of the catheter body 12 so that when the control handle 16 is rotated the tip section 14 will rotate in a corresponding manner.

The overall length and diameter of the catheter 10 may vary according to the application. A presently preferred catheter 10 has an overall length of about 48 inches. The outer diameter of the catheter body 12 is not critical, but is preferably no more than about 7 french. The inner surface of the outer wall 20 is preferably lined with a stiffening tube 22, which can be made of any suitable material that is less flexible than the outer wall 20, preferably nylon or polyimide. The stiffening tube 22, along with the braided outer wall 20, provides improved flexural and torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. A particularly preferred catheter 10 has an outer diameter of about 0.092 inch and a lumen 18 diameter of about 0.052 inch.

A preferred means for attaching the catheter body 12 to the tip section 14 is illustrated in FIG. 2. The proximal end of the tip section 14 comprises an outer circumferential notch 34 that receives the inner surface of the outer wall 20 of the catheter body 12. The tip section 14 and catheter body 12 are attached by glue or the like. Before the tip section 14 and catheter body 12 are attached, however, the stiffening tube 22 is inserted into the catheter body 12. The distal end of the stiffening tube 22 is fixedly attached near the distal end of the catheter body 12 by forming a glue joint with polyurethane glue or the like. Preferably a small distance, e.g., about 3 mm, is provided between the distal end of the catheter body 12 and the distal end of the stiffening tube 22 to permit room for the catheter body 12 to receive the notch 34 of the tip section 14. A force is applied to the proximal end of the stiffening tube 22, and, while the stiffening tube 22 is under compression, a first glue joint (not shown) is made between the stiffening tube 22 and the outer wall 20 by a fast drying glue, e.g., Super Glue®. Thereafter a second glue joint is formed between the proximal ends of the stiffening tube 22 and outer wall 20 using a slower drying but stronger glue, e.g., polyurethane.

With reference to FIGS. 4 and 5, the tip section 14 comprises a short section of flexible tubing 24 having four symmetrically arranged off-axis lumens therein. The flexible tubing 24 is made of a suitable non-toxic material that is preferably more flexible than the catheter body 20. A presently preferred material for the tubing 24 is braided polyurethane, i.e., polyurethane with an embedded mesh of braided stainless steel or the like. The outer diameter of the tip section 14, like that of the catheter body 12, is preferably no greater than about 7 french, more preferably about 6½ french or less.

It is understood that the number of lumens present in the tip section may vary and depends upon the intended use and design of the catheter 10. Lumens may be provided through which a variety of components, e.g., infusion tube, optic fiber, temperature sensing means, and/or an electromagnetic sensor, may extend. Various components, e.g., lead wires and temperature sensing means, may be combined in a single lumen if desired. In the embodiment depicted in FIGS. 4 and 5, first and second larger diametrically opposite off-axis lumens 26 and 27 and third and fourth smaller diametrically opposed off-axis lumens 28 and 29 are shown.

In the embodiment shown, electrode lead wires 31 extend through lumen 28 and a temperature sensor lead 30 extends through lumen 29. The electrode lead wires 31 are attached at their distal ends to ring electrodes and a tip electrode carried by the tip section. The temperature sensor lead 30 is connected at its distal end to a temperature sensor, e.g., a thermocouple or thermistor carried by the tip electrode. Preferred methods for mounting ring electrodes and a tip electrode on the tip section, as well as methods for attaching lead wires, are described in U.S. Pat. No. 5,827,278, which is incorporated herein by reference.

A puller wire 32 is provided within the catheter for deflecting the tip section 14. The puller wire 32 is anchored at its proximal end to the control handle 16 and is extended through the central lumen 18 in the catheter body 12 and into lumen 26 in the tip section.

The puller wire 32 is made of any suitable metal, typically stainless steel. Preferably the puller wire 32 has a coating, such as a coating of Teflon® or the like, that imparts lubricity to the puller wire. The puller wire 32 has a diameter preferably ranging from about 0.006 inch to about 0.0010 inch. The portion of the puller wire extending through the catheter body is surrounded by a compression coil 46. The compression coil 46 is made of any suitable metal, such as stainless steel, and is tightly wound on itself to provide flexibility, i.e., bending, but to resist compression. Such an arrangement is described, for example, in U.S. Pat. No. 5,827,278 issued Oct. 27, 1998, which is incorporated herein by reference.

Longitudinal movement of the puller wire 32 relative to the catheter body, which results in deflection of the tip section 14, is accomplished by a suitable manipulation of the control handle 16. Suitable control handles for use with the present invention are described, for example, in U.S. Pat. No. Re 34,502 entitled "Steerable Catheter" and application Ser. No. 08/982,064 entitled "Steerable Catheter With Electromagnetic Sensor" the disclosures of which are incorporated herein by reference.

Deflection, and particularly repeated deflection, of the tip section 14 results in a permanent deformation of the tip in the form of a residual tip curve. To eliminate the "residual tip curve" problem, a straightening element 50 is carried within lumen 27 of the catheter tip section 14. The straightening element 50 is made of a short section of a flexibly resilient material having shape memory and may be any suitable shape. In an un-flexed and unstressed state, i.e., not subject to any deflecting forces, the straightening element 50 is straight. The material of the straightening element 50 must be sufficiently resilient to bias the tip section 14 back to a straight arrangement after tip deflection. Accordingly, the straightening element 50 must be more resilient than the remainder of the tip section 14, i.e., the aggregate of the flexible tubing, puller wire, electrode lead wires and other components that might be present.

Preferred straightening elements include rods or wires having a circular cross-section and bars or plates having square or rectangular cross-sections. The diameter or cross-sectional width of the straightening element depends upon the material used. In a preferred embodiment, the straightening element 50 is made of a super-elastic nickel-titanium alloy which is a flexible yet highly resilient material. Such alloys typically comprises about 55% nickel and 45% titanium, but may comprise from about 54% to about 57% nickel with the balance being titanium. These alloys exhibit super-elastic behavior. When stressed, e.g., by bending, these materials are transformed from their austenitic phase to their martensitic phase. When the stress is removed, these materials return to their austenitic phase and spring back to their original shape.

A presently preferred super-elastic nickel-titanium alloy is marketed by U.S. Nitinol of Saratoga, Calif. under the trade name NITINOL. This material has excellent shape memory, together with ductility, strength, corrosion resistance, electrical resistivity and temperature stability. The straightening element 50 is preformed straight and it will substantially return to this shape in spite of any bending. This is what is meant by the term "shape memory" as used herein.

In a particularly preferred embodiment, the Nitinol wire used is preformed straight and has a circular cross-section. The diameter of the Nitinol wire is preferably in the range of about 0.010 inches to about 0.020 inches, and more preferably about 0.014 inches. It is preferred that the Nitinol wire be covered with a lubricious, non-conductive coating or sleeve such as Teflon® or the like.

In the embodiment shown, the distal end of the straightening element 50 is fixedly attached at the distal end of the tip section. The straightening element 50 extends proximally through the tip section 14 and into the distal end of the catheter body 12 wherein the proximal end of the straightening element 50 is fixedly attached to the flexible tubing 24 with polyurethane glue or the like. Alternatively, when a tip electrode is provided, the distal end of the straightening element 50 may be mounted in a blind hole in the tip electrode. In the latter arrangement, it is preferred that the straightening element be electrically isolated from the tip electrode. Other means for anchoring the straightening element 50 in the tip section 14 would be recognized by those skilled in the art and are included within the scope of the invention. It is presently preferred, albeit not critical to anchor the proximal end of the straightening element in the catheter body. Such an arrangement maximizes stability of the catheter tip section and eliminates any weak spots, i.e., areas of reduced stiffness, at or adjacent the proximal end of the tip section that might develop a residual curve or even kink upon bending. If desired, however, the straightening element may be carried only in the tip section. In an alternative embodiment, one end of the straightening element 50 is fixedly attached to the catheter 10, while the other end remains unattached and free floating. In the embodiment shown, the straightening element 50 is disposed in lumen 27 which is diametrically opposite the puller wire. If desired, the straightening element may be disposed in any lumen, including the same lumen as the puller wire 32.

When the catheter tip 14 is deflected by applying a force to the puller wire, the straightening element 50 deflects with the tip section 14. When the force is removed from the puller wire, the resiliency of the straightening element 50 biases the catheter tip section 14 back towards its initial straight position to reduce or eliminate "residual tip curve."

It is understood that any control handle and tip deflecting mechanism, including any mechanism for anchoring puller wires, may be used. Various tip deflection mechanisms and control handles are disclosed for example in U.S. Pat. Nos. Re. 34,502 and 5,897,529, both of which are incorporated by reference.

It is also understood that the present invention may be used with bi-directional or omni-directional catheters. Bi-directional catheters are those in which the tip is deflectable in two, typically opposing directions. Omni-directional catheters are those having three or more puller wires to enable deflection in all directions. Examples of such bi- and omni-directional catheters are disclosed in U.S. patent application Ser. No. 08/924,611, filed Sep. 5, 1997; U.S. patent application Ser. No. 09/130,359, filed Aug. 7, 1998; U.S. patent application Ser. No. 09/143,426, filed Aug. 28, 1998; and U.S. patent application Ser. No. 09/157,055, filed Sep. 18, 1998, all of which are incorporated herein by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A deflectable catheter comprising:
 a catheter body having proximal and distal ends and at least one lumen extending therethrough;
 a tip section comprising proximal and distal ends and at least one lumen extending therethrough, wherein the proximal end of the tip section is fixedly attached to the distal end of the catheter body;
 means for deflecting the tip section; and
 a straightening element carried in the tip section comprising a material having shape memory.

2. A catheter according to claim 1 wherein the deflecting means comprises a puller wire having a proximal end and a distal end and a control handle fixedly attached to the proximal end of the catheter body, the puller wire extending from the control handle, through the catheter body and into a lumen in the tip section, whereby manipulation of the control handle moves the puller wire relative to the catheter body, resulting in the deflection of the tip section.

3. A catheter according to claim 1 wherein the straightening element includes a proximal end and a distal end, the distal end of the straightening element being fixedly attached at the distal end of the tip section and the proximal end of the straightening element being fixedly attached at the distal end of the catheter body.

4. A catheter according to claim 1 wherein the straightening element includes a distal end, the distal end of the straightening element being fixedly attached to the distal end of the tip section.

5. A catheter according to claim 1 wherein the straightening element includes a proximal end, the proximal end of the straightening element being fixedly attached to the distal end of the catheter body.

6. A catheter according to claim 1 wherein the straightening element comprises a nickel titanium alloy.

7. A catheter according to claim 6 wherein the shape memory alloy is Nitinol.

8. A catheter according to claim 1 wherein the straightening element comprises a resilient plastic.

9. A catheter according to claim 1 wherein the straightening element has a circular cross-section.

10. A catheter according to claim 7 wherein the circular cross-section of the straightening element has a diameter in the range of about 0.010 inches to about 0.020 inches.

11. A catheter according to claim 7 wherein the circular cross-section of the straightening element has a diameter of about 0.014 inches.

12. A catheter according to claim 1 wherein the straightening element has a rectangular cross-section.

13. A catheter according to claim 2 wherein the tip section has a plurality of lumens, wherein the puller wire extends into one of the lumens and the straightening element extends into another of said lumens.

14. A catheter according to claim 1 wherein the puller wire is made of stainless steel.

15. A catheter according to claim 1 wherein the tip section is more flexible than the catheter body.

16. A catheter according to claim 1 wherein the proximal end of the straightening element is fixedly attached to one of the distal end of the catheter body and proximal end of the tip section.

17. A catheter according to claim 2 wherein the tip section comprises diametrically opposed off-axis lumens and the straightening element and the puller wire are mounted in the diametrically opposed off-axis lumens.

18. A deflectable catheter comprising:

a catheter body having proximal and distal ends and at least one lumen extending therethrough;

a tip section comprising proximal and distal ends and a plurality of lumens extending therethrough, wherein the proximal end of the tip section is fixedly attached to the distal end of the catheter body;

a control handle fixedly attached to the proximal end of the catheter body;

a puller wire having a proximal end and a distal end and a control handle fixedly attached to the proximal end of the catheter body, the puller wire extending from the control handle, through the catheter body and into a lumen in the tip section, whereby manipulation of the control handle moves the puller wire relative to the catheter body, resulting in the deflection of the tip section; and a straightening element having a proximal end fixedly attached to the distal end of the catheter body and extending into a lumen in the tip section, other than the lumen carrying the puller wire, the straightening element comprising a material having shape memory.

* * * * *